United States Patent [19]

Armstrong et al.

[11] Patent Number: 5,411,175
[45] Date of Patent: May 2, 1995

[54] CARTRIDGES, DEVICES AND METHODS FOR DISPENSING LIQUIDS

[75] Inventors: John C. Armstrong, Milton, Mass.; Frank Venus, Jr., Merrimac, N.H.

[73] Assignee: New England Pharmaceuticals, Inc., North Easton, Mass.

[21] Appl. No.: 27,518

[22] Filed: Mar. 8, 1993

[51] Int. Cl.⁶ .............................................. B67D 5/00
[52] U.S. Cl. .............................................. 222/83.5
[58] Field of Search ................ 222/82, 83, 83.5, 88, 222/95, 145, 105, 327, 386; 604/201, 204, 294; 239/276, 309

[56] References Cited

U.S. PATENT DOCUMENTS

| | | | |
|---|---|---|---|
| 2,373,774 | 4/1945 | Murnane | 222/83 |
| 2,696,212 | 12/1954 | Dunmire | 604/204 |
| 2,888,924 | 6/1959 | Dunmire | 604/201 |
| 3,904,083 | 9/1975 | Little | 222/83.5 |
| 4,214,584 | 7/1980 | Smirnov et al. | 604/201 |
| 4,336,907 | 6/1982 | Cummins | 239/309 |
| 4,605,398 | 8/1986 | Herrick | 604/300 |
| 4,623,337 | 11/1986 | Maurice | 604/298 |
| 4,779,768 | 10/1988 | St. Amand | 222/209 |
| 4,792,334 | 12/1988 | Py | 604/301 |
| 4,871,094 | 10/1989 | Gall et al. | 222/386 |
| 4,927,062 | 5/1990 | Walsh | 222/420 |
| 4,946,452 | 8/1990 | Py | 604/301 |
| 4,966,581 | 10/1990 | Landau | 604/72 |
| 4,981,479 | 1/1991 | Py | 604/302 |
| 5,048,727 | 9/1991 | Vlasich | 222/209 |
| 5,085,651 | 2/1992 | Py | 604/298 |
| 5,133,702 | 7/1992 | Py | 604/302 |
| 5,154,702 | 10/1992 | Foyil | 604/212 |
| 5,204,108 | 4/1993 | Illum | 424/434 |
| 5,215,079 | 6/1993 | Fine et al. | 128/200.14 |
| 5,219,101 | 6/1993 | Matkovich et al. | 222/189 |
| 5,273,190 | 12/1993 | Lund | 222/83 |

FOREIGN PATENT DOCUMENTS 2020425  7/1990  Canada .

Primary Examiner—Andres Kashnikow
Assistant Examiner—Philippe Derakshani
Attorney, Agent, or Firm—Linda M. Buckley

[57] ABSTRACT

A cartridge for providing a liquid to be dispensed and devices for and methods of dispensing a liquid from such cartridges are disclosed. Such cartridges include a container having the liquid to be dispensed disposed therein, the container including a pierceable section and a piercer capable of piercing the pierceable section. The piercer is internal to the container for the liquid thereby making it possible to maintain the sterility of the liquid until the moment of use.

15 Claims, 5 Drawing Sheets

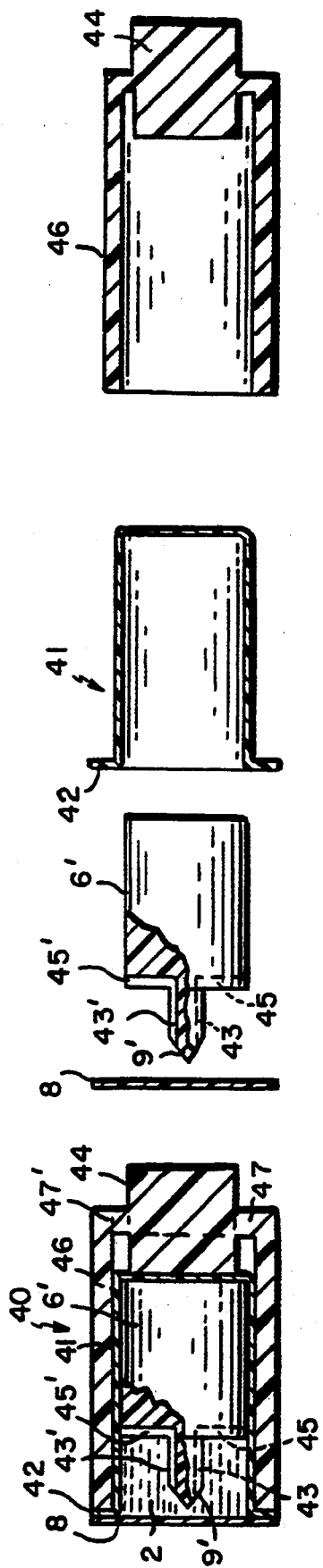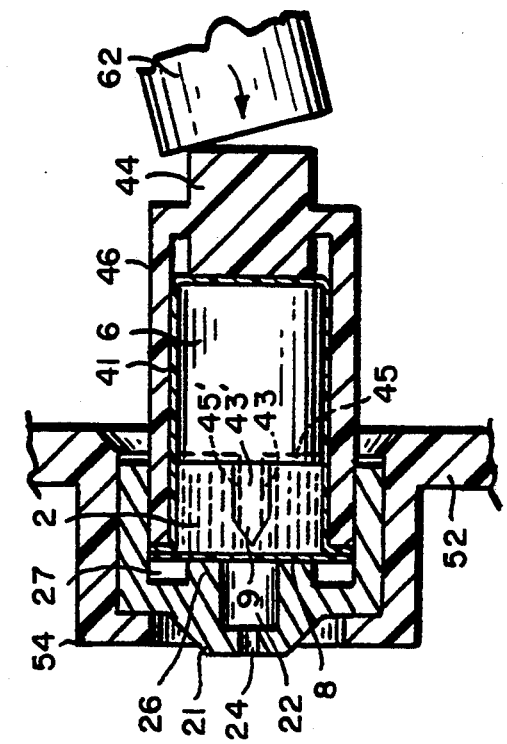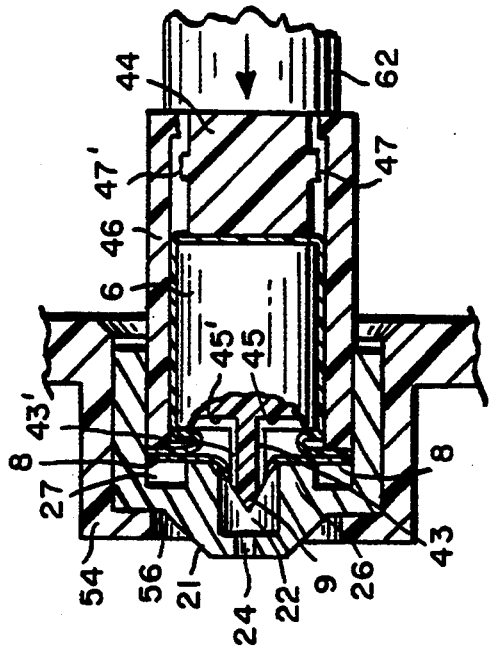

CARTRIDGES, DEVICES AND METHODS FOR DISPENSING LIQUIDS

BACKGROUND OF THE INVENTION

This invention relates to cartridges for providing a liquid to be dispensed and to devices for and methods of dispensing a liquid from such cartridges, such as a liquid containing medicaments and drugs. In a preferred embodiment, such liquids are dispensed to the eye of a user.

A variety of devices for dispensing liquid are known. Exemplary devices for dispensing a liquid to the eye of a user are disclosed in, e.g., U.S. Pat. Nos. 3,087,656; 3,788,528; 4,623,337; 4,811,866; and 4,925,065. Included among these devices are both multi-dose and single-dose devices.

Multi-dose devices pose problems with product sterility, e.g., when the device is used repeatedly to dispense liquid to the eye. Although practically all such devices and their contents are sterile before they are opened for use, not only is the product within the dispenser no longer sterile after opening but there is danger of contamination of the contents by the user, as well as cross-contamination where several people, e.g., family members, use the same dispensing device.

Some commercially available single-dose devices are sold with instructions that the user discard the device after one use. However, many such single dosage units hold over 350 $\mu l$ of liquid and dispense on an average 50 $\mu l$ of liquid per drop, leaving more than 300 $\mu l$ of liquid after a single use or about 250 $\mu l$ when both eyes are treated. The user is often reluctant to discard a device still more than half full, resulting in reuse of a single-dose device. Reuse not only negates the purpose of single-dose dispensing but also greatly increases the danger of contamination and product deterioration, since single-dose devices, once opened, typically cannot be reclosed for a tight seal.

Maintaining sterility of the product to be dispensed is not only necessary to prevent contamination but is also a desirable feature to reduce or eliminate the need for a preservative.

In addition to the sterility problems inherent in known devices for dispensing liquid to the eye of a user, most such devices are neither easy nor convenient to use. Anyone who has ever had to apply drops of liquid to the eye is aware of the difficulty and inconvenience typically experienced with currently available devices. Frequently, the drop misses the targeted eye and the procedure must be repeated. Furthermore, such devices suffer deficiencies both in volume of liquid delivered as well as reproducibility of the amount of liquid dispensed. Both of these deficiencies translate into dosage problems when the liquid contains a medication.

Volume of liquid dispensed by dispensing devices on the market today, typically droplets of liquid in excess of 35 $\mu l$ and some as high as 56 $\mu l$, results in waste. Since the eye can only hold 25 $\mu l$, see, e.g., Keister et al., *Journal of Pharmaceutical Sciences*, 80 (1991) 50–53, anything in excess of 35 $\mu l$ will be wasted. Even in cases where cost is not a factor, droplet size can be important, e.g., in cases where the efficiency of a medication is greatly enhanced with a droplet size of about 10 $\mu l$ (See, e.g., Keister et al., supra).

Since presently known devices for the delivery of liquids to the eye suffer disadvantages which include sterility maintenance, imprecise delivery, and ease of use alternative dispensing devices are being sought.

SUMMARY OF THE INVENTION

The present invention provides cartridges for providing a liquid to be dispensed, as well as devices and methods for dispensing liquids from such cartridges. Although in a preferred embodiment of the present invention the liquid is dispensed to the eye of a user, the present invention can be used to deliver liquid to, e.g., the nose or ear of a user.

Cartridges of the present invention for providing a liquid comprise a container having the liquid to be dispensed disposed therein, wherein the container comprises a pierceable section and a piercer capable of piercing the pierceable section. The piercer is internal to the container for the liquid thereby making it possible to maintain the sterility of the liquid until the moment of use. The pierceable section of such containers is provided by conventional materials, such as pierceable plastics, plastic laminates, and plastic metal laminates.

Piercers for use in the present invention may be manufactured independently of the container or as an integral part of the container. In some embodiments, the piercer is moved towards and pierces the pierceable section of the container. In yet other embodiments, the pierceable section is moved towards and is pierced by the piercer.

In preferred embodiments of the present invention, the cartridges are provided with a head space of air between the liquid and the pierceable section. The air in the head space compresses readily thereby facilitating movement of the piercer and/or the pierceable section. In some embodiments, the air or gas in the head space also facilitates dispensing of the liquid. In embodiments wherein the cartridge is manufactured without a head space, the piercer is positioned with respect to the pierceable section so as to limit the degree of movement necessary to achieve piercing of the seal.

In some embodiments of the present invention, the piercer is provided with a sealing lip to provide an interference or sealing fit with the inner wall of the container to minimize or prevent the liquid from flowing between the piercer and the inner wall of the container. The sealing lip allows the piercer to be constructed with clearance between the piercer and container to reduce friction, while the sealing lip, which is preferably short and very flexible, provides a seal against leakage past the piercer. In such embodiments, the piercer may be hollow and open at the end distal to the pierceable section. When a sealing lip is not provided, i.e., the fit with the inner wall of the container is not an interference fit, the piercer is closed at the end distal to the pierceable section to minimize the volume of liquid which can flow away from the pierceable section. In embodiments wherein the piercer is not an integral part of the container, the piercer is dimensioned so as to fit within the container, and where a sealing lip is present, so that the sealing lip provides an interference fit with the inner wall of the container.

The volume of liquid dispensed from the cartridge is determined by the size of the container, piercer and head space. By appropriately dimensioning these components, the desired volume can be readily achieved. In all embodiments, any residual liquid is taken into account in formulating the appropriate volume to provide the desired dosage.

The cartridges of the present invention are intended for use with any device capable of dispensing the liquid therefrom. As will be apparent to the skilled artisan, the cartridges of the present invention may be used with various dispensing devices that properly orient the cartridge with respect to the eye, nose or ear of a user and that also provide for appropriate movement to enable the piercer to pierce the pierceable section. As mentioned above, movement of the piercer towards the pierceable section and vice versa is included within the scope of the present invention.

In a preferred embodiment, a spray head is provided for use in conjunction with the cartridges of the present invention. In operation, the spray head fits over the cartridge at the pierceable section thereof and is provided with an orifice through which the liquid to be dispensed is directed when the piercer pierces the pierceable section of the cartridge. The spray head together with the cartridge is sometimes hereinafter referred to as the cartridge assembly.

The present invention also provides dispensing devices for receiving a cartridge assembly and dispensing the liquid therefrom. In one preferred embodiment, the dispensing device is provided with a receptacle for receiving the cartridge assembly at the spray head. The receptacle is provided with an opening aligned with the opening in the spray head for dispensing the liquid. Preferred dispensers are also provided with a member for positioning the device at the eye of the user so that the liquid will strike the eyeball of the user as it is dispensed.

In other embodiments of the present invention, not shown in the Figures, the spray head is incorporated into the body of the dispenser.

The cartridges, devices and methods of the present invention overcome many of the disadvantages associated with known devices and methods of dispensing liquid to the eye of a user. One important advantage resides in the fact that the cartridge cannot be used again, thereby obviating the reuse problem, and resultant loss of sterility associated with many units on the market which are intended as single-dose units. Another important advantage is total protection of the liquid until the moment of use. Loss of sterility is avoided, because the liquid to be dispensed is not exposed to the air except during actual usage. A cartridge that has been damaged, e.g., is defective at the area of the pierceable section or develops a leak, would not work to dispense the liquid because the liquid would be forced out through the leak before the pierceable section could be pierced or sufficient pressure be generated to effectively discharge the liquid.

Another important advantage is that, unlike current eye-droppers where dosage depends upon the amount of squeezing action, the devices of the present invention dispense a discrete volume each time, regardless of the manner in which the actuator is depressed. Even when a conventional eye-dropper is manipulated very carefully, the smallest droplet that will free fall from the tip is approximately 35 $\mu l$ of water. This is due to the effect of surface tension between the liquid and the tip of the dropper and also the liquid remaining inside the tip.

The devices of the present invention dispense liquid under pressure, e.g., by piston action of the piercer or by simple displacement of the liquid and, in some embodiments, with an assist from the expanding air or gas in the head space. This in part, enables the successful dispensing of droplets as small as 6 $\mu l$. It is believed that the devices of the present invention can be used for those medications where a droplet size of 10 $\mu l$ or less is a necessary requirement.

The devices of the present invention require little or no coordinatioon on the part of the user. This is an important advantage for users who experience difficulties in applying eye drops due to physical infirmities, such as arthritis and other disabling conditions. The devices of the present invention enable the user to more easily and accurately dispense the required dosage to the eye.

The convenience in use provided by the devices of the present invention is readily apparent. Since gravity is not necessary for dispensing, the unit can be operated from any direction, upright, horizontal or even from a downward position. Because the dispenser is positioned directly over the eye socket and the liquid is dispensed from the center axis, the droplet is directed very accurately onto the eyeball.

The present invention provides benefits in terms of economy as well as sterility and droplet size. Dispensers for use with the aforesaid cartridge assemblies can be used repeatedly, thus enabling the user to purchase only the cartridges or the cartridge assemblies containing the liquid to be dispensed. Moreover, the dispenser can be readily molded from inexpensive plastic in high volume thereby further reducing the cost. In addition, because of the accuracy and efficiency with low volumes, a further saving is effected with the product.

BRIEF DESCRIPTION OF THE DRAWINGS

In the drawings:

FIG. 6 shows one embodiment of a holder in accordance with the present invention.

FIG. 7 shows another preferred embodiment of a container for holding liquid to be dispensed in accordance with the present invention.

FIG. 8 shows a piercer in accordance with the present invention.

FIG. 9 show a pierceable seal for use with the container shown in FIG. 7.

FIG. 10 is another embodiment of a cartridge in accordance with the present invention for holding a liquid to be dispensed.

FIG. 11 shows a cross-sectional view of yet another embodiment of the device in accordance with present invention.

FIG. 12 is a cross-sectional view of the device shown in FIG. 11 wherein the liquid has been dispensed.

DESCRIPTION OF THE INVENTION

Although the liquid dispensing cartridges, devices and methods of the present invention are primarily illustrated by those which have been adapted for delivery of liquids to the eye of a user, it will be appreciated by those skilled in the art that such devices may also be adapted for dispensing liquid to, e.g., the nose or the ear of a user.

Figures 1, 2:
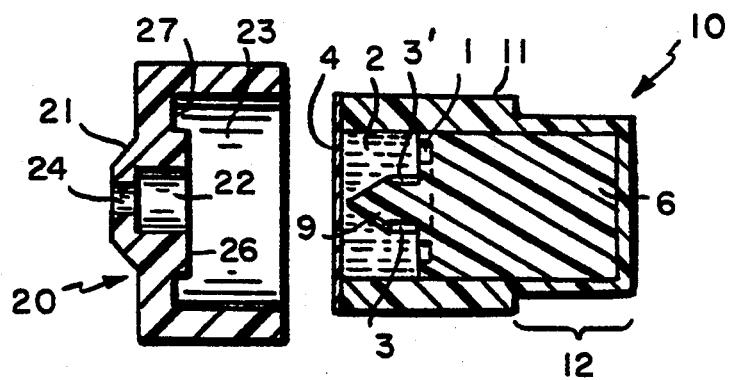
FIG. 1 is a cross-sectional view of one embodiment of a cartridge in accordance with the present invention for holding a liquid to be dispensed.
FIG. 2 is a cross-sectional view of one embodiment of a spray head in accordance with the present invention.
Figure 3:
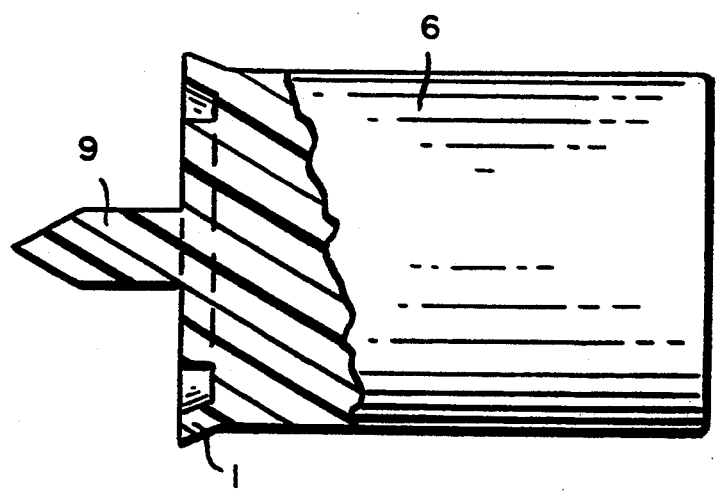
FIG. 3 is an enlarged cross-sectional view of a piercer similar to that shown in FIG. 1.
Figure 14:
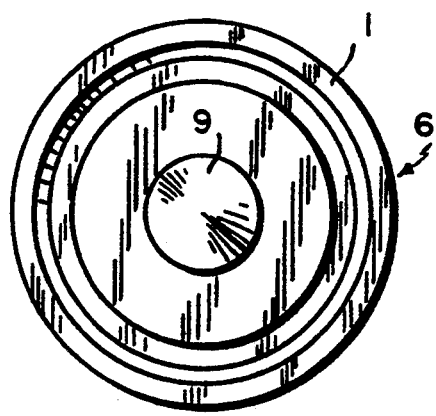
FIG. 14 is a front plan view of the piercer shown in FIG. 3.

Referring now to FIG. 1 there is shown one embodiment of a cartridge 10 in accordance with the present invention for containing a liquid to be dispensed. Cartridge 10 comprises container 11 for containing a liquid to be dispensed, the container 11 comprising the liquid 2, pierceable section 4, piercer 6 capable of piercing pierceable section 4 when moved into contact therewith, and moveable, e.g., collapsible or foldable, section 12. Piercer 6 shown in FIG. 3 is not an integral part of container 11 but rather is manufactured separtely. Piercer 6 comprises a cylinder having projecting axially from the front end thereof a smaller cylindrical pointed member 9.

FIG. 10 shows another preferred embodiment of a cartridge 40 in accordance with the present invention for providing a liquid to be dispensed. FIGS. 6 through 9 show the components of cartridge 40.

Figure 16:
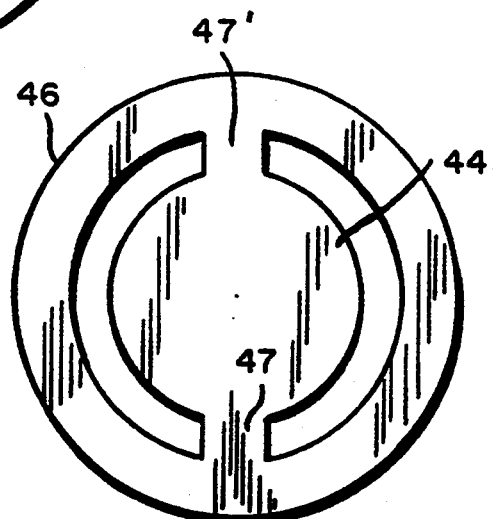
FIG. 16 is a rear view of the container shown in FIG. 6.

In this embodiment, cartridge 40 comprises flexible container 41 shown in FIG. 7, piercer 6' shown in FIG. 8, pierceable seal 8 shown in FIG. 9 for sealing flexible container 41, once piercer 6' and the liquid 2 to be dispensed are disposed therein, and holder 46 shown in FIG. 6 for receiving flexible container 41. Flexible container 41 is provided with flange 42. Referring again to FIG. 6, holder 46 is provided with plug 44 positioned in holder 46 by means of webs 47,47' shown in FIGS. 12 and 16. Pierceable seal 8 and flange 42 are welded together and also to the rim of holder 46, preferably in one operation.

In FIG. 2 there is shown one embodiment of a spray head 20 for use in conjunction with cartridge 10 of FIG. 1 and cartridge 40 of FIG. 10. A spray head having a cartridge disposed therein is hereinafter sometimes referred to as a cartridge assembly. Spray head 20 comprises spray tip 21 and socket 23 dimensioned to receive a cartridge at its pierceable section. Socket 23 is provided with section 22 for receiving the pointed member 9,9' of piercer 6,6'. As shown in FIG. 1, spray tip 21 is provided with orifice 24 which, when a cartridge is disposed in socket 23, is open to the atmosphere and to the pierceable section of the cartridge. Socket 23 is provided with annular projection 26.

Figure 4:
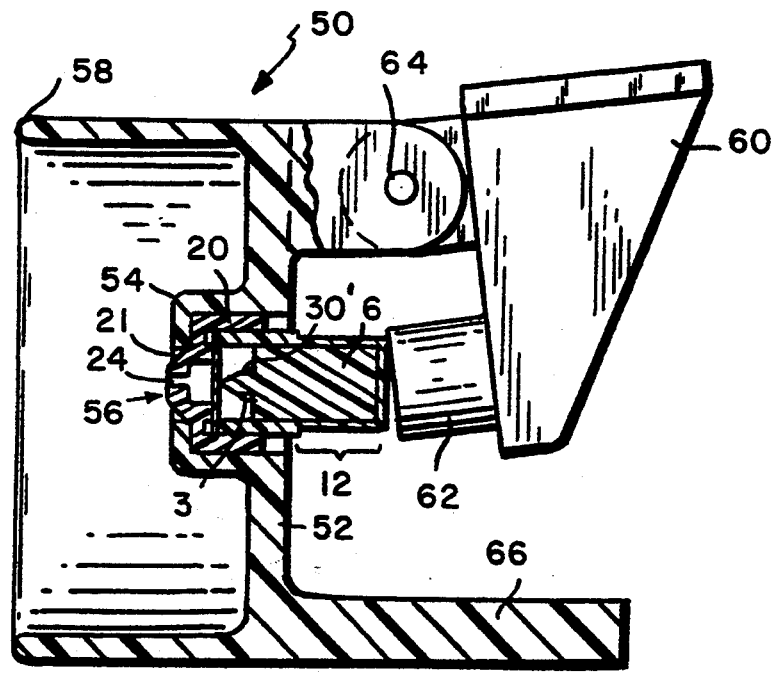
FIG. 4 is a cross-sectional view of the container and spray tip shown in FIGS. 1 and 2 respectively in one embodiment of a dispenser in accordance with the present invention.

The present invention also provides dispensing devices for receiving a cartridge assembly and for dispensing the liquid therefrom. In FIG. 4 is shown dispenser 50 having disposed therein spray head 20 and cartridge 10. Although cartridge 10 is shown in FIG. 4, cartridge 40 could be substituted therefor. In FIGS. 11 and 12 is shown a partial view of dispenser 50 having cartridge 40 disposed therein.

Referring back to FIG. 4, dispenser 50 comprises body member 52 which is provided with receptacle 54 for receiving a cartridge assembly. Receptacle 54 is adapted to engage spray head 20 and is provided with opening 56 which is aligned with orifice 24 in spray tip 21. As the liquid is dispensed, it passes through orifice 24 and opening 56. Opening 56 is dimensioned larger than orifice 24 in spray tip 21 to minimize impingement on dispenser 50 of the liquid to be dispensed.

As shown in FIG. 4, body member 52 also comprises a projecting front member 58 for positioning opening 56 of receptacle 54 and orifice 24 of spray tip 21 in front of the user's eye. Projecting number 58 is adapted to conform to the shape of the facial area surrounding the eye socket of a user and, in a preferred embodiment, is similar in shape to the common eye cup.

Body member 52 further comprises actuating member 60 movably connected thereto by hinge 64. Actuating member 60 is provided with projecting member 62 which abuts the end of cartridge 10 or 40 when the cartridge assembly is disposed in receptacle 54, i.e., loaded into dispenser 50. Body member 52 also comprises base member 66.

To load the dispenser, actuating member 60 is lifted up to clear receptacle 54 for positioning of spray head 20 and cartridge 10 or 40. Spray head 20 and cartridge 10 or 40 is placed into receptacle 54, with spray head 20 inward, and projecting member 62 of actuating member 60 is allowed to drop freely against the projecting end of cartridge 10 or 40.

Figure 5:
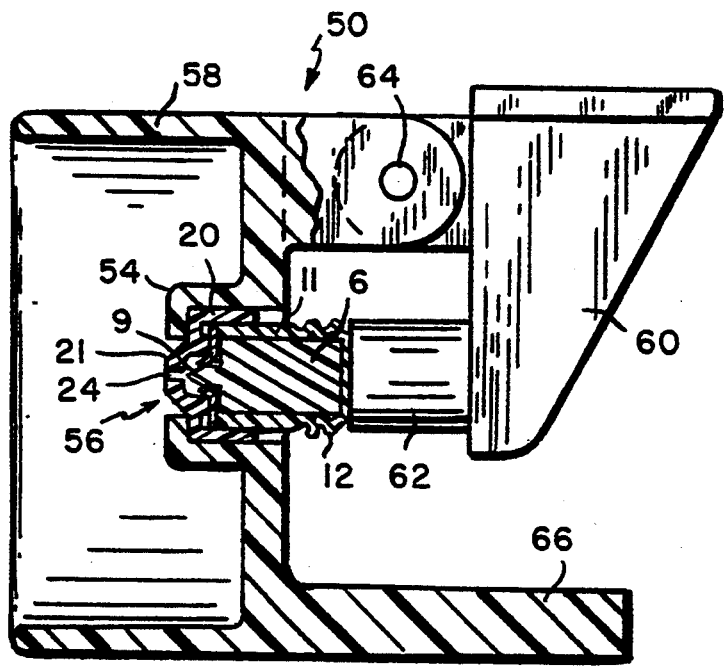
FIG. 5 is a view of the device shown in FIG. 4, wherein the liquid has been dispensed.

In use, the device is clasped at the top of actuating member 60 and at base member 66 between the thumb and forefinger and projecting member 58 is placed around the eye socket of the user to position orifice 24 and opening 56 at the eye of the user. A quick press by the user on actuator 60 causes the liquid to be dispensed through orifice 24 in spray tip 20 and opening 56 in receptacle 54. In this operation, projecting member 62 of actuating member 60 engages the moveable section of cartridge 10 or 40 and moves it and the piercer towards the pierceable section, thereby causing the piercer to pierce the pierceable section as shown in FIGS. 5 and 12. In the embodiments shown, the liquid is dispensed by the piston action of piercer 6,6' and, in embodiments wherein the head space is provided between the liquid and the pierceable section, with an assist by expansion of compressed air or gas in the head space.

As shown in FIGS. 11 and 12, when cartridge 40 and spray head 20 are disposed in dispenser 50, actuating member 60 is moveable towards and projection 62 is contactable with moveable plug 44. A quick press by the user on actuating member 60 causes projection 62 to engage moveable section 44 and move it forward, breaking webs 47,47' thereby enabling actuating member 60 to move plug 44 towards pierceable seal 8. This causes piercer 6' to move forward and pierce pierceable seal 8 as shown in FIG. 12. As pierceable seal 8 is pierced, liquid 2 is dispensed through orifice 24 in spray tip 21 and opening 56 in receptacle 54.

After actuation, the actuating lever 60 is simply lifted out of the way and the spent cartridge assembly is pulled out of socket 22.

Figure 13:
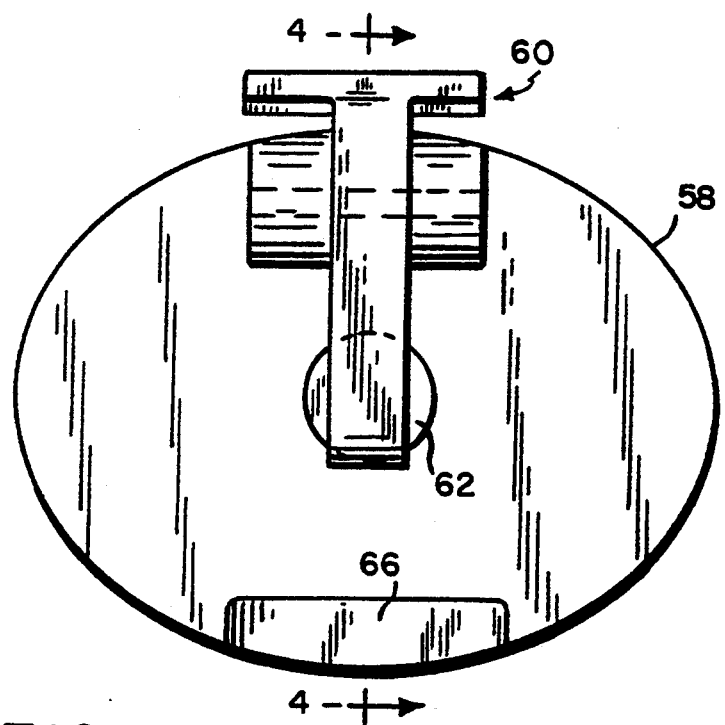
FIG. 13 is a rear view of the dispenser shown in FIG. 4.

A rear view of dispenser 50 is shown in FIG. 13.

Figure 17:
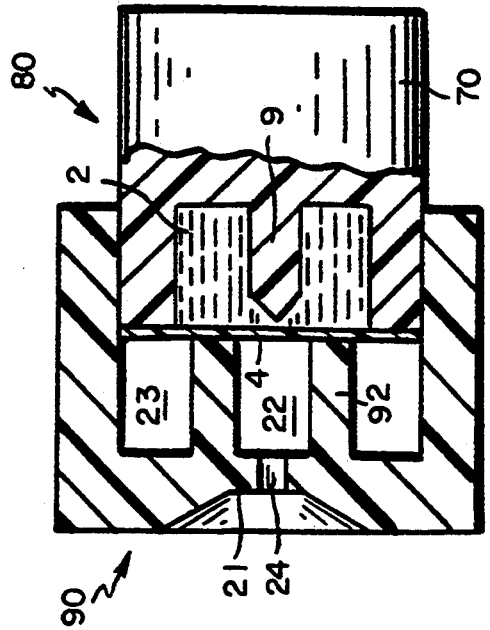
FIG. 17 is a cross-sectional view of another preferred cartridge assembly of the present invention.
Figure 18:
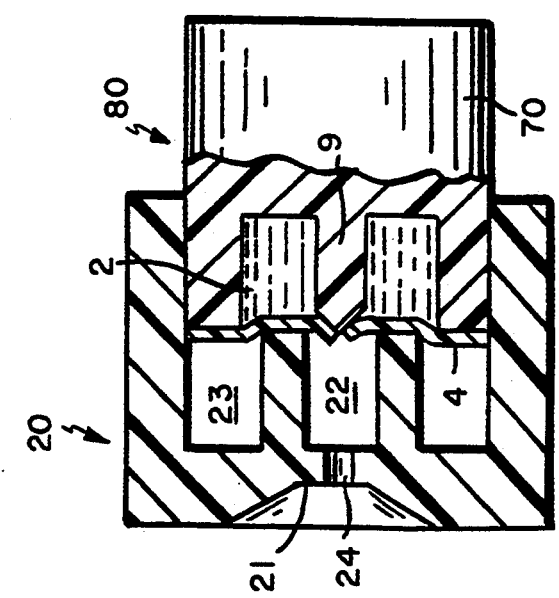
FIG. 18 shows the device of FIG. 17 as the piercer is piercing the pierceable section.
Figure 19:
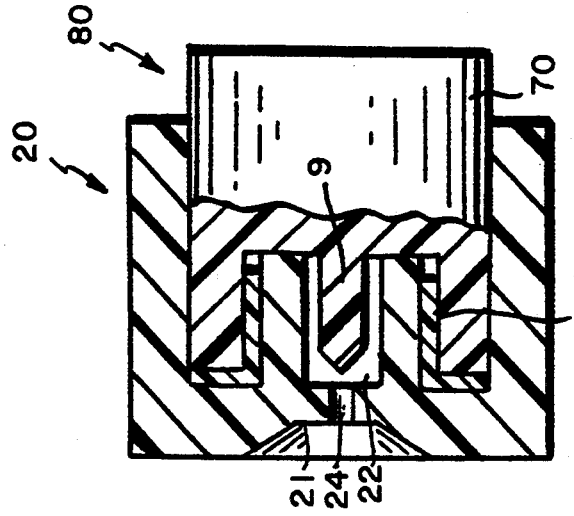
FIG. 19 shows the device of FIG. 18 wherein the piercer has completely pierced the pierceable section and the liquid has been dispensed.
Figure 20:
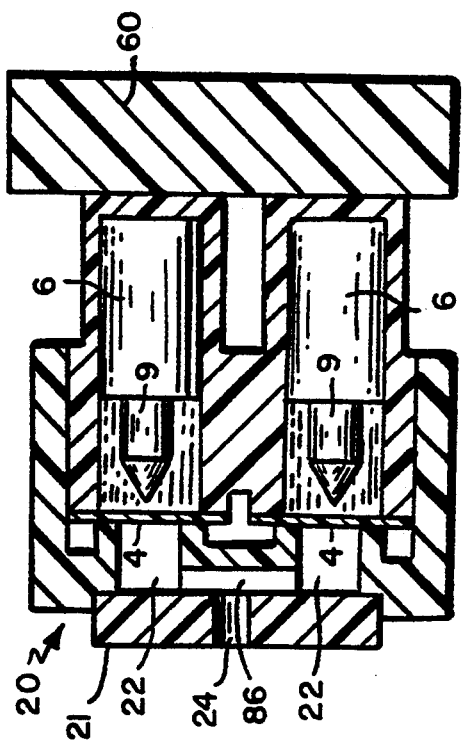
FIG. 20 shows a dual cartridge assembly in accordance with the present invention.

In yet other preferred embodiments of the present invention, the pierceable seal is moveable towards the piercer. One such embodiment is shown in FIGS. 17 to 19. Piercer 70 is formed as an integral part of container 80. As shown in FIG. 17, the cartridge is disposed in spray head 90 before actuation. Spray head 90 is similar in structure to spray head 20, similar structures are given the same identifying numbers. During actuation, annular projection 92 of socket 23 engages pierceable section 4 and causes piercing thereof as shown in FIGS. 19 and 20. Liquid is dispensed through orifice 24 in spray tip 21.

As shown in FIG. 20, spray heads in accordance with the present invention can be configured to receive, two or more cartridges, where it is desired to dispense two or more liquids simultaneously. In such embodiments, the volume of the cartridges can be varied to dispense various proportions of liquids. Structures in FIG. 20 similar to those shown in FIGS. 1 and 2 are given the same numbers. Connecting member 86 is provided, to receive the liquids after piercing of the cartridges and to lead the liquids to common terminal orifice 24 in spray tip 21.

In the embodiments shown in FIGS. 5 and 12, the force exerted by actuating member 60 is transmitted directly to the back of the piercer and hydrostatically to the pierceable section, forming a seal against annular projection 26 of spray head 20 resulting in a sealing action between the pierceable section and the face of projection 26 inside spray head 20. See, FIGS. 10 and 11. Annular projection 26 of spray head 20 acts as a stop for the pierceable section to prevent it from bulging out too far and thereby requiring excessive travel for the piercer.

In some embodiments, annular recess 27 as shown in FIG. 2 is provided between annular projection 26 and the inner diameter of socket 23. Annular recess 27 provides clearance to accept the rough surface formed in embodiments wherein the pierceable section is welded to container 11 and holder 46. Although a proper seal can be effected without annular recess 26, it is preferred.

Two preferred embodiments of piercers 6 and 6' in accordance with the present invention are shown in the figures. Such piercers are preferably cylindrical and may be solid or hollow, and in some embodiments open at the end opposite the cylindrical pointed member.

Referring to FIG. 1, pointed member 9 of piercer 6 is optionally provided with axial flow channels, 3,3' to enhance dispensing of the liquid. For example, in embodiments of cartridge 10 wherein pierceable section 4 comprises a single ply of very flexible plastic film, a very close fit, e.g., 0.004 to 0.005 inches, between pointed member 9 and section 22 of spray tip 20 is preferred to limit extrusion of plastic film into section 22. In such embodiments, axial flow channels 3,3' provide a flow path between piercer 6 and the plastic film for the liquid 2 to be dispensed. In embodiments wherein pierceable section 4 comprises a stiffer material, such as a multi-laminate or plastic-aluminum laminate, which does not stretch and is more easily pierced without tearing, as close a fit between piercer 6 and section 22 of socket 23 is not typically important. As shown in FIGS. 1 and 3, piercer 6 further comprises annular sealing lip 1 to minimize back flow of liquid around piercer 6 and into container 11 when piercer 6 is moved forward to pierce pierceable section 4. The sealing lip 1 has an interference fit with the inner diameter of container 11, e.g., about 0.005 inch.

Figure 15:
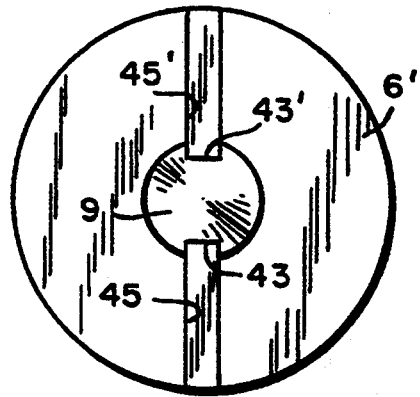
FIG. 15 is a front view of the piercer shown in FIG. 8.

In embodiments which include a very flexible container such as assembly 40 shown in FIG. 10, it is preferred that piercer 6' be provided with axial flow channels 43,43' on pointed member 9' and radial flow channels 45,45' positioned on the front end of the piercer in alignment with axial flow channels 43,43' as shown in FIG. 8. A top view of piercer 6' showing these flow channels is shown in FIG. 15.

In preferred embodiments of cartridges of the present invention, a head space is left between liquid 2 and pierceable section 4,8. In such embodiments, when piercer 6,6' is moved towards pierceable section 4,8, air in the head space is compressed, and, as pierceable section 4,8 is pierced, liquid 2 is dispensed through orifice 24 in spray tip 20 and opening 56 in receptacle 54, in part through expansion of the compressed air in the head space.

For example, in the embodiment shown in FIGS. 6–12, as force is applied by the lever action of actuating member 60 to moveable section 44 of holder 46, moveable section 44 and piercer 6' move together towards pierceable seal 8 as the front end of flexible container 41 collapses as shown in FIG. 12. This movement is facilitated, because the air or gas in the head space compresses very readily.

As mentioned previously, air compressed within the cartridges of the present invention serves another function, in addition to allowing the piercer to move more readily forward and pierce the pierceable section or seal. The sudden release of pressure as the pierceable section or seal is pierced causes the compressed air to expand, acting as a propellent to help project the liquid to be dispensed out of the cartridge. Therefore, in embodiments provided with a head space, even when actuating lever 60 is depressed rather slowly, the sudden decompression of air will provide the necessary propulsion to the liquid to be dispensed. Although a head space of air or gas is not required to discharge the liquid, it is preferred because a lower and smoother operating force and more consistent droplet formation is provided thereby.

The cartridges, spray heads and devices of the present invention are made from conventional materials and by conventional techniques known to those of ordinary skill in the art. The material selected will depend in part upon compatibility with the liquid to be dispensed, intended method of sterilization, permeability of the material and moldability of the material. In other words, the appropriate material will depend upon the application or intended use, as well as ease of manufacturing. To ensure simple manufacturing, it is advantageous to use a readily processable material.

Some preferred materials for use in the present invention are listed below. The container 10 and Holder 46: High density polyethylene, low density polyethylene, polypropylene and polyester; The Piercer: Nylon, high density polyethylene, polyester and polypropylene; The Flexible Container 41: Low density polyethylene, polyester, polypropylene, poly vinyl chloride and laminates of various plastics; The Pierceable Section (Mono-Layer): Polyethylene, polypropylene, polyester, poly vinyl chloride and coated aluminum; The Pierceable Section (Multi-Layer): Combination of two or more of the foregoing; and The Dispenser: Acrylic, polycarbonate, polyester and polypropylene.

Containers for holding the liquid to be dispensed, are provided with a pierceable section. In one embodiment, the pierceable section is provided by sealing the container with a conventional pierceable material, such as a plastic or metal film, using methods known to those skilled in the art. Desired characteristics for such sealing materials, such as resistance to the passage of moisture, are readily apparent to the skilled routineer.

In the assembly shown in FIG. 10, it is possible to seal flexible container 41 before it is placed in holder 46. However, it is generally preferred to seal container 41 and to affix flange 42 to holder 46 in a single operation.

A cartridge similar to that shown in FIG. 10 can be prepared as follows. Container 41 for the liquid to be dispensed is fitted with a flange 42 at the open end. In a preferred embodiment container 41 is a flexible plastic bag thermo-formed from a flat sheet of plastic in a manner well known to the industry. Container 41 is assembled into holder 46, a hollow tube of plastic, similar to the material of bag 40, with the closed end inside holder 40 and flange 42 abutting the rim of holder 46. Holder 46 is also provided with plug 44 and webs 47,47'.

Piercer 6' comprises a solid circular rod slightly less in diameter than the inside of container 41. Piercer 6' is flat at one end and fitted with a cylindrical pointed member 9' smaller in diameter than piercer 6' and terminating in a sharp conical point, at the other end. Piercer 6' was dropped into container 41, flat end toward the closed end of container 41.

The diameter and length of cylindrical extension 9' is sized so that the space between it and the inside diameter of container 41 provides sufficient volume to contain the liquid to be dispensed, residual, and a head space, i.e., a slight amount of air or inert gas. The sharp point is dimensioned to come to slightly below the rim of container 41 and holder 46 to prevent accidental piercing of pierceable seal 8. Container 41 is sealed with pierceable seal 8 comprising a circular disc of thin plastic the same diameter as flange 42 and of a material similar to that of the container 40 and holder 46. Pierceable seal 8 and flange 42 are welded together and also to the rim of holder 46, either by heat or ultrasonics, preferably in one operation.

A spray head 20 is then assembled to cartridge 40 at the pierceable seal 8 by frictional engagement with the outer diameter of holder 46, and seated firmly against the pierceable seal 8. The assembly is then loaded into dispenser 50 for actuation.

In the embodiment shown in FIGS. 1-5, container 11 is closed at one end with projection 12. Projection 12 is thin walled to enable it to collapse. Piercer 6 is inserted, flat end inward as before, to abut against the closed end of container 40. After filling, pierceable seal 4 is welded directly to the rim of container 40 and spray head 20 fitted as before. This cartridge assembly is loaded into dispenser 50.

In the embodiment shown in FIGS. 17 to 19, the piercer is molded as an integral part of container 80.

In one preferred embodiment of a spray head in accordance with the present invention, the inside edge of section 22 is blunt or slightly radiused so as not to act as a cutting die, resulting in material from pierceable section 4,8 being sheared off and plugging orifice 24 in spray tip 21. However, a close fit between the piercer 6,6' and the inside diameter of socket 22 is preferred, i.e., no more clearance than necessary to allow room for the flap of pierceable material formed when the seal is pierced.

In another preferred embodiment, the depth of socket 22 is sufficient to provide approximately 0.015 inch clearance between the inlet to orifice 24 and the tip of cylindrical pointed member 9,9' at its maximum forward position. Because of the close fit desired between the tip and socket 22, axial flow channels 3,3' or 43,43' running the length of cylindrical pointed member tip 9,9' and into the conical tip are provided as shown in the figures. Flow channels are not present in all embodiments of the present invention. In cases where such channels are absent, the fit between tip 9,9' and socket 22 provides about 0.010 inch clearance all around to allow flow of liquid. This eliminates the need for flow channels and, in some cases, also produces a more uniform droplet.

In preferred embodiments, spray head 20 is provided with cartridge 10,40 and the cartridge assembly is disposable. In another embodiment of the present invention, not shown, spray head 20 is integral with dispenser 50. However, in this embodiment, the dispenser has to be cleaned and sterilized after each usage because of the residue of liquid left in the spray head. Accordingly, in commercial use it is preferred to provide a spray head with each cartridge.

The dispenser 50 is preferably made of a clear, transparent and rigid plastic.

In some embodiments of the present invention, dispenser 50 is adapted to receive multiple containers of liquid to be dispensed.

It will be apparent to the skilled artisan in light of the teachings of the present invention that configurations of the cartridges, spray heads, and dispensers other than those shown may be utilized without departing from the spirit and scope of the invention. The configuration and dimensions of cartridges, spray heads and dispensers for use in the present invention will be dictated by the intended use.

The cartridge is dimensioned to hold the desired amount of liquid to be dispensed and the spray head is dimensioned to receive the cartridge.

In embodiments for dispensing liquid to the eye of a user, the dispenser is adapted to conform to the shape of the facial area surrounding the eye socket, and, preferably, dimensioned to be easily hand held. In embodiments for dispensing liquid from a cartridge of the present invention to the nose or ear, the dispensers will be configured differently.

As is amply illustrated by the various embodiments in accordance with the present invention described herein, by following the teachings of the present invention one of ordinary skill in the art can vary the disclosed cartridges, spray heads and devices by utilizing ordinary skill in the art to meet the demands of a particular liquid, particular delivery area, particular user and so forth.

It is understood that the embodiments described herein are for illustrative purposes only and that the various modifications or changes in light thereof that will be suggested to persons skilled in the art are to be included in the spirit and purview of this application and the scope of the approved claims.

What is claimed is:

1. A cartridge for providing a liquid to be dispensed, the cartridge comprising a container for holding the liquid, the container having the liquid disposed therein and comprising, a solid piercer and a pierceable section, wherein the piercer is capable of piercing the pierceable section said piecer disposed in the liquid prior to piercing the pierceable section.

2. The cartridge of claim 1, wherein the cartridge further comprises a head space.

3. The cartridge of claim 1, wherein the piercer is integral with the container.

4. The cartridge of claim 1, further comprising a moveable section capable of movement to bring the pierceable section and the piercer together to effect piercing of the pierceable section.

5. The cartridge of claim 4, wherein a section of the container opposite the pierceable section comprises the moveable section, and the moveable section is engageable with the piercer to provide movement towards and piercing of the pierceable section.

6. The cartridge of claim 4, wherein the moveable section comprises the pierceable section.

7. A dispenser adapted for receiving at least one cartridge in accordance with claim 1, the dispenser comprising a member for moving the piercer and the pierceable section together to effect piercing thereof, and a member for dispensing the liquid to an intended delivery target.

8. A cartridge in accordance with claim 1, wherein the solid piercer is provided with at least one axial flow channel.

9. A cartridge for providing a liquid to be dispensed comprising:
   a. a flexible container for holding the liquid, the container having the liquid disposed therein and comprising a solid piercer and a pierceable section, the piercer being capable of piercing the pierceable section; and
   b. a holder having the flexible container disposed therein to provide access to the pierceable section, the holder comprising a member moveable towards the pierceable section, wherein the moveable member is engageable with the piercer to provide movement towards and piercing of the pierceable section.

10. A cartridge assembly for providing a liquid to be dispensed comprising:
    a. a cartridge for providing a liquid to be dispensed, the cartridge comprising a container for holding a liquid, the container having the liquid disposed therein and comprising a solid piercer and a pierceable section, wherein the piercer is capable of piercing the pierceable section; and
    b. a spray head positioned adjacent the pierceable section, wherein the spray head comprises a spray tip, the spray tip having an orifice open to the atmosphere and to the pierceable section;
    whereby when the pierceable section is pierced, the liquid is dispensed through the orifice in the spray tip.

11. A dispenser adapted for receiving at least one cartridge assembly in accordance with claim 10, the dispenser comprising a member for moving the piercer and the pierceable section together to effect piercing thereof, and a member for dispensing the liquid to an intended delivery target.
    whereby when the pierceable section is pierced, the liquid is dispensed through the orifice in the spray tip to the intended delivery target.

12. A dispenser in accordance with claim 11, wherein the member for dispensing the liquid to an intended delivery target comprises a member to position the spray tip at the intended delivery target.

13. A dispenser for receiving at least one cartridge assembly in accordance with claim 10, the dispenser comprising:
    a. a body member comprising a receptacle open at one end for receiving the spray head of the cartridge assembly, the interior of the receptacle being adapted to engage the spray head and being provided with an opening which is aligned with the orifice in the spray tip;
    b. a projecting front member connected to the body member for positioning the opening in the receptacle and the orifice in the spray tip in front of a user's eye; and
    c. an actuating member movably connected to the body member and, when the cartridge assembly is in the receptacle, capable of engaging the member moveable towards the seal and moving it towards the pierceable section;
    whereby when the moveable member is moved towards the pierceable section, the piercer is moved towards and pierces the pierceable section seal, and, as the pierceable section is pierced, the liquid is dispensed through the orifice in the spray tip and the opening in the receptacle.

14. A dispenser adapted for receiving at least one cartridge for providing a liquid to be dispensed,
    wherein the cartridge comprises a container for holding the liquid, the container having the liquid disposed therein and comprising a piercer and a pierceable section, wherein the piercer is capable of piercing the pierceable section, and
    wherein the dispenser comprises (i) a member for moving the piercer and the pierceable section together to effect the piercing thereof, and (ii) a dispensing member for dispensing the liquid to an intended delivery target, the dispensing member comprising a spray head adapted to receive the cartridge at the pierceable section, the spray head comprising a spray tip having an orifice open to the atmosphere and to the pierceable section.

15. A dispenser in accordance with claim 14, wherein the member for dispensing the liquid to the intended deliver target further comprises:
    a member to position the spray tip at the intended delivery target,
    whereby when the pierceable section is pierced, the liquid is dispensed through the orifice in the spray tip to the intended delivery target.

* * * * *